(12) United States Patent
Di Virgilio et al.

(10) Patent No.: US 8,575,419 B2
(45) Date of Patent: Nov. 5, 2013

(54) FEMININE HYGIENE ARTICLE WITH WAVY PATTERNS

(75) Inventors: Maurizio Di Virgilio, Chieti (IT);
Cornelia Ecker, Schwalbach (DE);
Ivano Gagliardi, Pescara (IT); Peter Charles Mason, Jr., Maineville, OH (US); Vincenzo Partenza, Elice (IT);
Paolo A. Veglio, Pescara (IT)

(73) Assignee: The Procter and Gamble Company, Cincinnati, OH (US)

( * ) Notice: Subject to any disclaimer, the term of this patent is extended or adjusted under 35 U.S.C. 154(b) by 281 days.

(21) Appl. No.: 11/732,588

(22) Filed: Apr. 4, 2007

(65) Prior Publication Data
US 2008/0249495 A1    Oct. 9, 2008

(30) Foreign Application Priority Data

Apr. 7, 2006    (EP) .................................... 06112392

(51) Int. Cl.
*A61F 13/472*    (2006.01)
*A61F 13/511*    (2006.01)
*A61F 13/533*    (2006.01)

(52) U.S. Cl.
USPC .................................. 604/380; 604/385.101

(58) Field of Classification Search
USPC ......................................... 604/380, 385.101
See application file for complete search history.

(56) References Cited

U.S. PATENT DOCUMENTS

| | | | | |
|---|---|---|---|---|
| 2,788,003 A | * | 4/1957 | Morin | 604/366 |
| 3,881,490 A | * | 5/1975 | Whitehead et al. | 604/366 |
| D240,564 S | * | 7/1976 | Whitehead et al. | D24/125 |
| 4,057,061 A | * | 11/1977 | Ishikawa | 604/375 |
| 4,079,739 A | * | 3/1978 | Whitehead | 604/365 |
| D274,362 S | * | 6/1984 | Whitehead | D24/125 |
| 4,623,340 A | * | 11/1986 | Luceri | 604/385.05 |
| 4,795,453 A | * | 1/1989 | Wolfe | 604/385.101 |
| 5,004,465 A | * | 4/1991 | Ternstrom et al. | 604/385.25 |
| H1376 H | * | 11/1994 | Osborn et al. | 604/361 |
| 5,503,076 A | * | 4/1996 | Yeo | 101/483 |
| D403,764 S | | 1/1999 | Lynard et al. | |
| 5,897,541 A | * | 4/1999 | Uitenbroek et al. | 604/358 |
| 5,993,431 A | * | 11/1999 | McFall et al. | 604/385.24 |
| D430,292 S | | 8/2000 | Orschel et al. | |
| D434,144 S | * | 11/2000 | Anderson | D24/124 |
| 6,165,319 A | * | 12/2000 | Heath et al. | 162/112 |

(Continued)

FOREIGN PATENT DOCUMENTS

| | | |
|---|---|---|
| EP | 1842512 A1 | 10/2007 |
| JP | 4274548 | 6/2009 |
| WO | WO 02/07662 A1 | 1/2002 |
| WO | WO 03/053313 A2 | 7/2003 |

OTHER PUBLICATIONS

European Search Report dated Aug. 9, 2006.

*Primary Examiner* — Melanie Hand
*Assistant Examiner* — Paula Craig
(74) *Attorney, Agent, or Firm* — Andrew J. Hagerty; Megan C. Hymore; Amanda T. Berry

(57) ABSTRACT

A feminine hygiene article for external use having on their body-facing surface at least one embossed wavy pattern and at least one non-embossed, preferably colored, wavy pattern. The embossed and non-embossed wavy patterns are chosen with specific geometric parameters so that a slight lateral or longitudinal shift does not affect the overall appearance of the body-facing surface.

11 Claims, 9 Drawing Sheets

(56) References Cited

U.S. PATENT DOCUMENTS

| | | |
|---|---|---|
| 6,171,432 B1 | 1/2001 | Brisebois et al. |
| 6,264,640 B1 * | 7/2001 | Sutton ................... 604/385.18 |
| 6,264,784 B1 | 7/2001 | Menard et al. |
| 6,521,811 B1 * | 2/2003 | Lassen et al. ............... 604/378 |
| 6,608,236 B1 * | 8/2003 | Burnes et al. ............... 604/378 |
| 6,617,490 B1 * | 9/2003 | Chen et al. .................. 604/380 |
| 6,719,742 B1 * | 4/2004 | McCormack et al. ... 604/385.01 |
| 6,893,525 B1 * | 5/2005 | Schmidt et al. .............. 156/209 |
| 7,048,726 B2 * | 5/2006 | Kusagawa et al. ....... 604/385.28 |
| 7,195,810 B1 * | 3/2007 | Schmidt et al. .............. 428/156 |
| 7,786,340 B2 * | 8/2010 | Gagliardi et al. ............ 604/361 |
| 8,148,597 B2 * | 4/2012 | Gubernick et al. .......... 604/361 |
| 2001/0007065 A1 * | 7/2001 | Blanchard et al. ........... 604/369 |
| 2001/0021838 A1 * | 9/2001 | Mizutani et al. ........ 604/385.28 |
| 2003/0109839 A1 | 6/2003 | Costea et al. |
| 2003/0114809 A1 | 6/2003 | Gagliardi et al. |
| 2003/0114811 A1 * | 6/2003 | Christon et al. ............. 604/362 |
| 2003/0187418 A1 | 10/2003 | Kudo et al. |
| 2004/0015145 A1 * | 1/2004 | Miura et al. ................. 604/367 |
| 2004/0122386 A1 * | 6/2004 | Mocadlo ...................... 604/359 |
| 2004/0127883 A1 | 7/2004 | Cowell et al. |
| 2004/0170813 A1 | 9/2004 | Digiacomantonio et al. |
| 2004/0176734 A1 * | 9/2004 | Rasmussen et al. .......... 604/380 |
| 2004/0253892 A1 * | 12/2004 | Baker et al. .................. 442/327 |
| 2004/0267220 A1 * | 12/2004 | Hull et al. .................... 604/380 |
| 2006/0149202 A1 * | 7/2006 | Cardin et al. ............ 604/385.04 |
| 2007/0087169 A1 * | 4/2007 | McFall ......................... 428/172 |
| 2007/0191802 A1 * | 8/2007 | Gubernick et al. ...... 604/385.01 |
| 2007/0293834 A1 * | 12/2007 | Miura et al. ............. 604/385.01 |
| 2008/0249494 A1 * | 10/2008 | Digiacomantonio et al. 604/378 |

\* cited by examiner

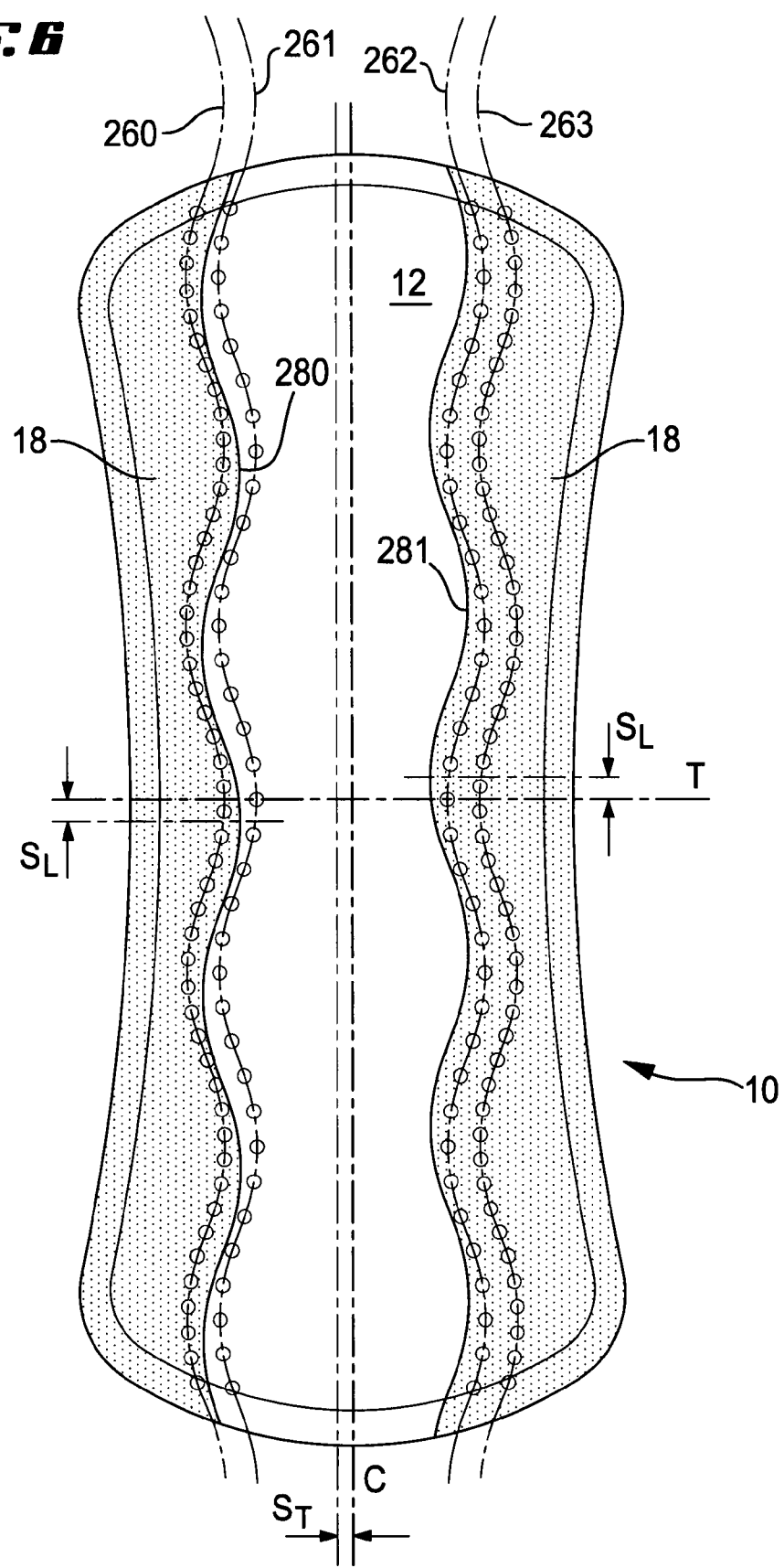

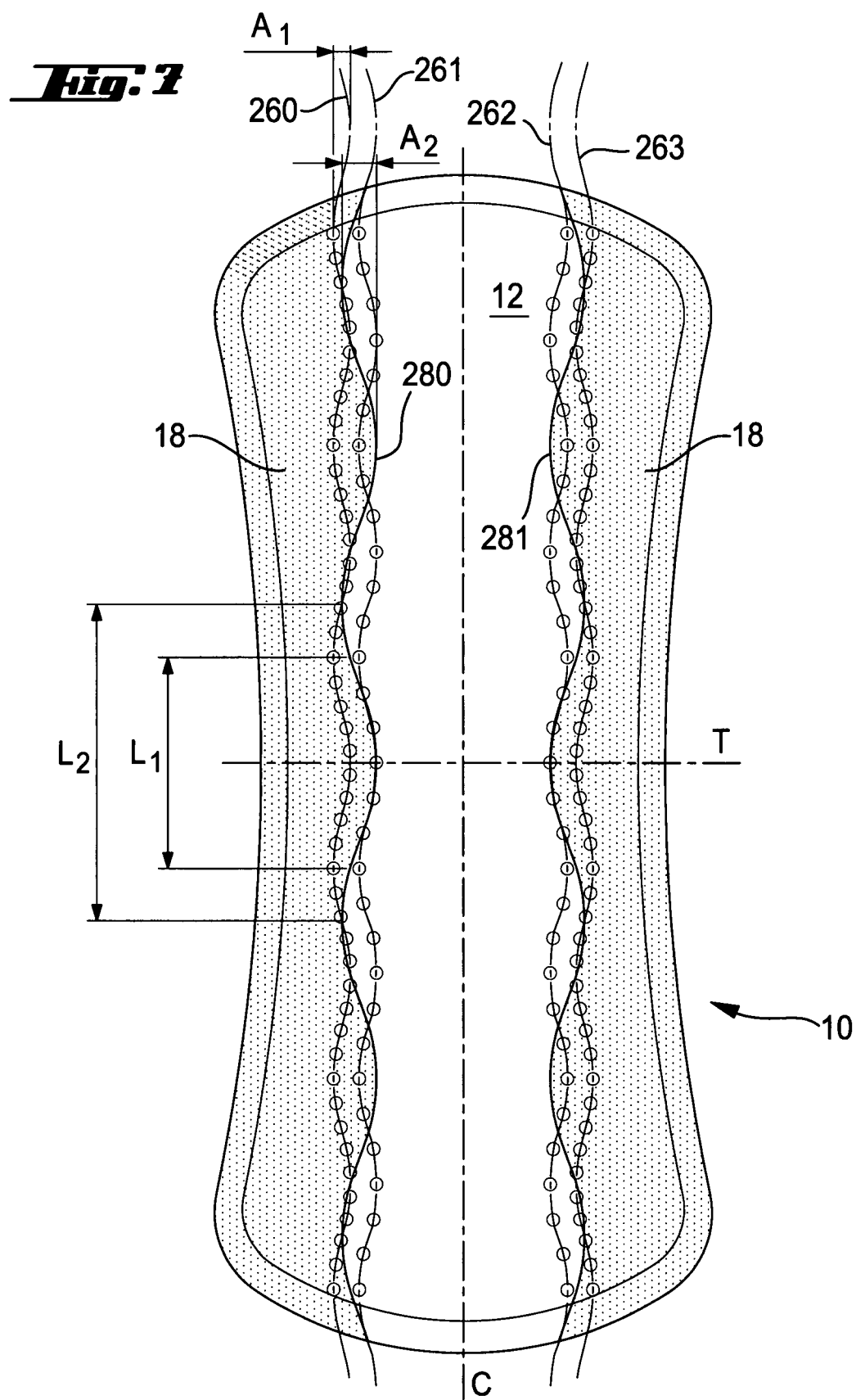

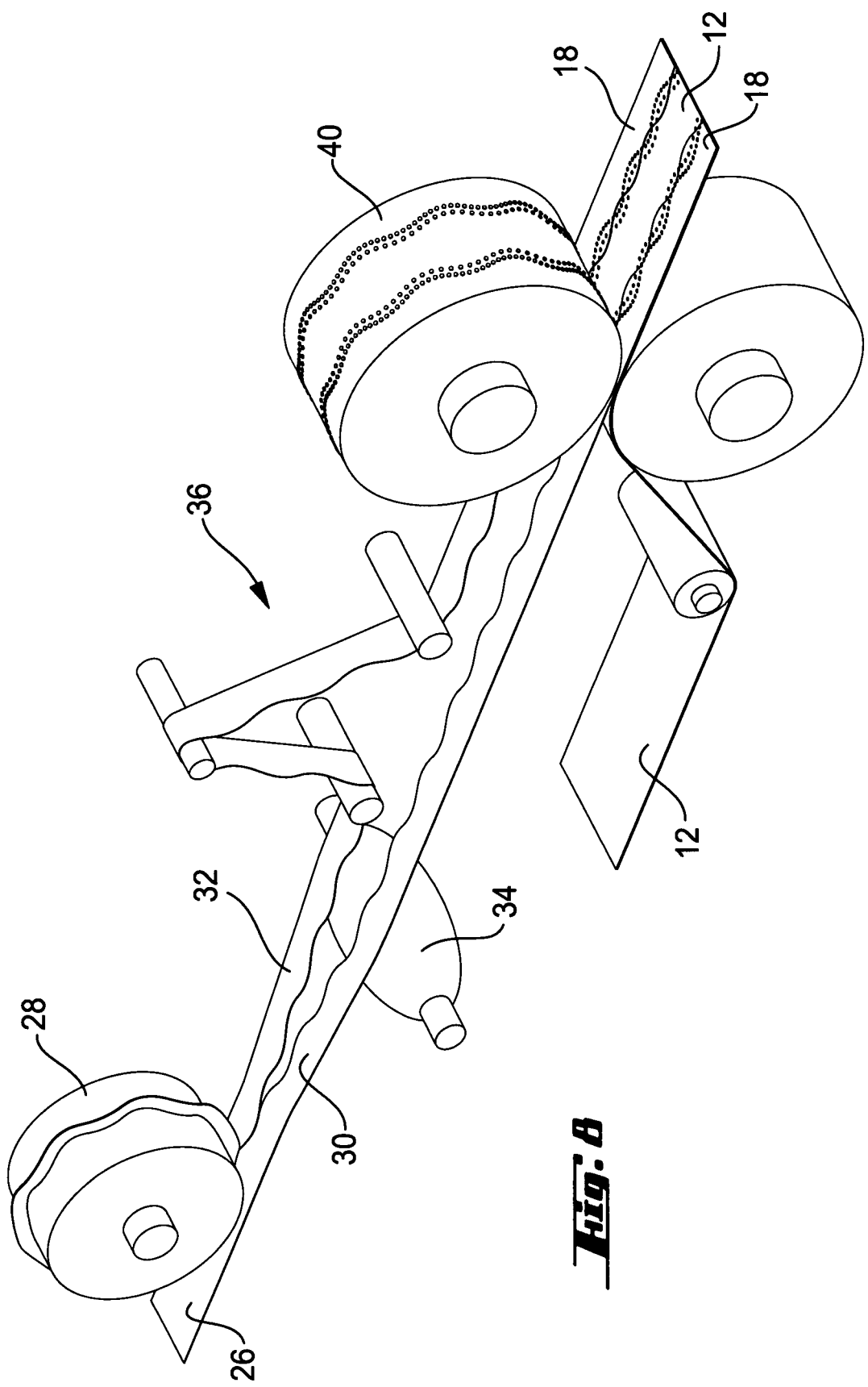

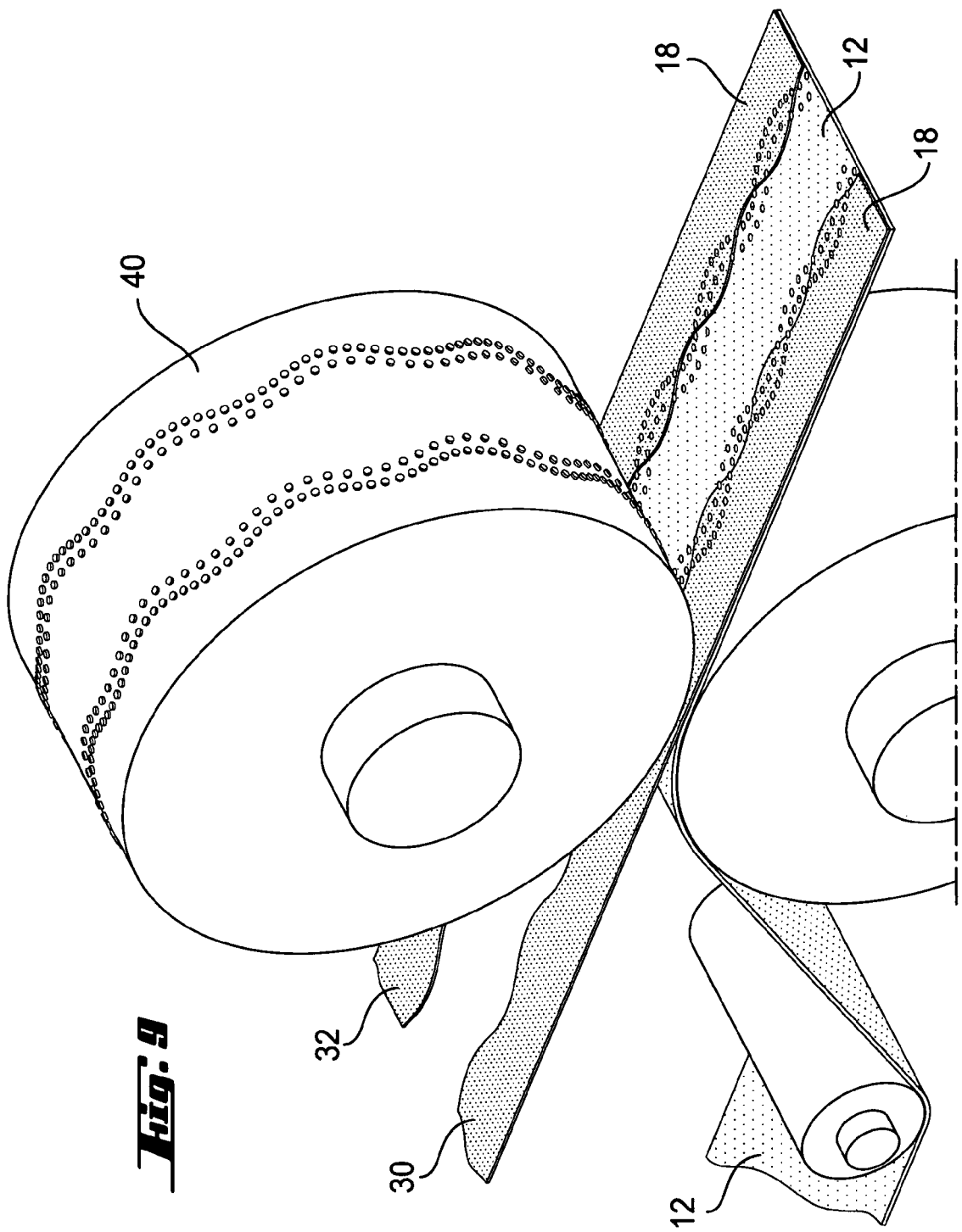

FEMININE HYGIENE ARTICLE WITH WAVY PATTERNS

This application claims priority to European Patent Application No. 06112392.3 filed Apr. 7, 2006.

FIELD OF THE INVENTION

The invention relates to feminine hygiene articles for external use. More specifically the invention relates to feminine hygiene articles having on their body-facing surface an embossed wavy pattern and a non-embossed wavy pattern.

BACKGROUND OF THE INVENTION

Feminine hygiene articles such as sanitary napkins are used by women during their menstrual periods to receive and contain blood discharges from the vagina. These absorbent sanitary articles are normally placed between the user's crotch and her undergarment. In addition to collecting menses, these articles may also be used to protect the wearer's undergarment from other bodily fluid such as urine in the case of light incontinence of the user.

These articles are generally flat and comprise a body-facing surface and an opposite garment-facing surface. Many commercial products are decorated on their body-facing surface with embossments. Various embossed decorative patterns have been proposed, see for example U.S. D403,764, U.S. D430,292. It has also been proposed to use non-embossed decorations, in particular colored pattern, on the body-facing surface of such articles for aesthetic reasons or to convey a functional benefit. For example in WO 03/53313 a concentric multi-tone non-embossed combination is used in the center of the body-surfacing to convey an impression of depth and absorbency to the user. In WO 02/07662, dark non-embossed absorbent articles are proposed to be worn with dark underwear to be less conspicuous.

Only few products have been marketed showing on their body-facing surface at the same time an embossed pattern and a non-embossed pattern. One reason for this is the additional cost and complexity of applying two patterns of different natures in a coordinated way ("registration"). For example, because embossment and ink are applied in different process steps, it is easy for slight variations or displacements in the horizontal, vertical or both directions to occur during the high-speed manufacturing process. This is not a problem when only one decorative pattern is applied, as the slight shift away from the ideally desired position will generally not be noticed by the user. However when two kinds of patterns such as a non-embossed (e.g. colored) and an embossed pattern are applied, they are normally expected to have some degree of correspondence to provide an aesthetic effect. An accidental displacement of one or the other pattern will be easily recognized by a consumer because these patterns will no longer match each others in the originally desired way. Continuously monitoring and correcting the position of the patterns however significantly raise the cost and manufacturing complexity of the process.

There is therefore a need for a feminine hygiene article comprising on its body-facing surface an embossed pattern and a non-embossed pattern that provide the appearance or appeal of registration but do not require continuous registration.

The inventors have found that instead of continuously monitoring and correcting the position of the patterns during manufacture, it was possible to achieve results having for the user the appeal of registration even after slight horizontal or vertical displacements of any or both of the patterns. This result is obtained by applying a wavy embossed pattern and a wavy non-embossed pattern having certain geometric parameters. In these conditions, it was found that the visual appeal for the users (the appearance of registration) is kept even when slight shifts occur.

SUMMARY OF THE INVENTION

The invention relates to a feminine hygiene article comprising a body-facing surface, a longitudinal centerline and a transverse centerline, wherein the longitudinal centerline has a length L, and the transverse centerline has a width W. The body-facing surface comprises:

i) an embossed wavy pattern, the embossed wavy pattern comprising waves having a maximum wavelength L1 and a maximum amplitude A1, and ii) a non-embossed wavy pattern, the non-embossed wavy pattern comprising waves having a maximum wavelength L2 and a maximum amplitude A2, wherein each of the values of the ratio L1/L and L2/L are independently less than 1, and wherein each of the values of the ratio A1/W and A2/W are independently less than 0.3.

The invention is also for a method of manufacturing a feminine hygiene article comprising two lateral topsheet strips having a wavy edge, the lateral topsheet strips being symmetrically disposed across the longitudinal centerline C, the method comprising the steps of:

i) providing a band of material, ii) cutting this band of material in its middle along a wavy cut pattern to form two strips of material each having a wavy edge, iii) de-phasing one of the strips in relation to the other by half a phase so that the strips appear to be mirror image of each other, iv) placing the strips of material over the topsheet, iv) attaching the strips to the topsheet so that they form lateral topsheet strips.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and in which:

FIG. 6 is a top view of the body-facing surface of the embodiment of FIG. 1 wherein a slight shift in the longitudinal and transversal direction occurred.

FIG. 7 is a top view of the body-facing surface of another embodiment of the invention.

FIG. 8 is a schematic view of an implementation of a process for making lateral topsheet strips having a regular wavy cut and being mirror image of each other.

FIG. 9 is a close-up view of the embossing unit of FIG. 8.

DETAILED DESCRIPTION OF THE INVENTION

Feminine Hygiene Article

As used herein, the term "feminine hygiene articles" refers to the type of disposable absorbent articles externally worn by women for menstrual and/or light incontinence control. These articles are commonly referred to as pads, sanitary napkins or sanitary towels. These articles have generally flat surfaces and are typically held in place adjacent the user's externally-visible genitalia (i.e., the pubic region) by the user's undergarment on which they are affixed via adhesive or other joining means.

The term "body-facing surface" refers to the side of the absorbent article facing the body of the user when in use. The "garment-facing surface" is the opposite surface of the article.

Figure 1:
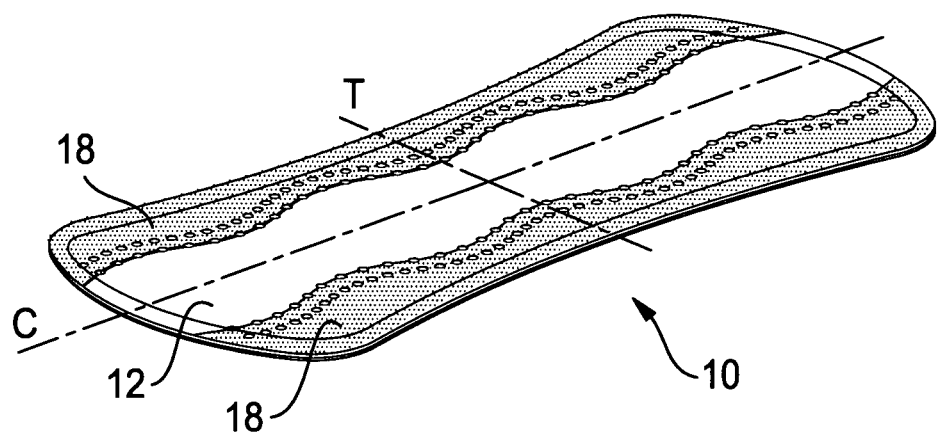
FIG. 1 is a perspective view of an exemplary feminine hygiene article according to the invention.

FIG. 1 shows a perspective view of the body-facing surface of a feminine hygiene article 10 according to the invention, herein represented as a liner. The articles of the invention will normally have a generally flat body-facing surface. However the feminine hygiene articles of the invention are not limited to a particular design construction.

Figure 2:
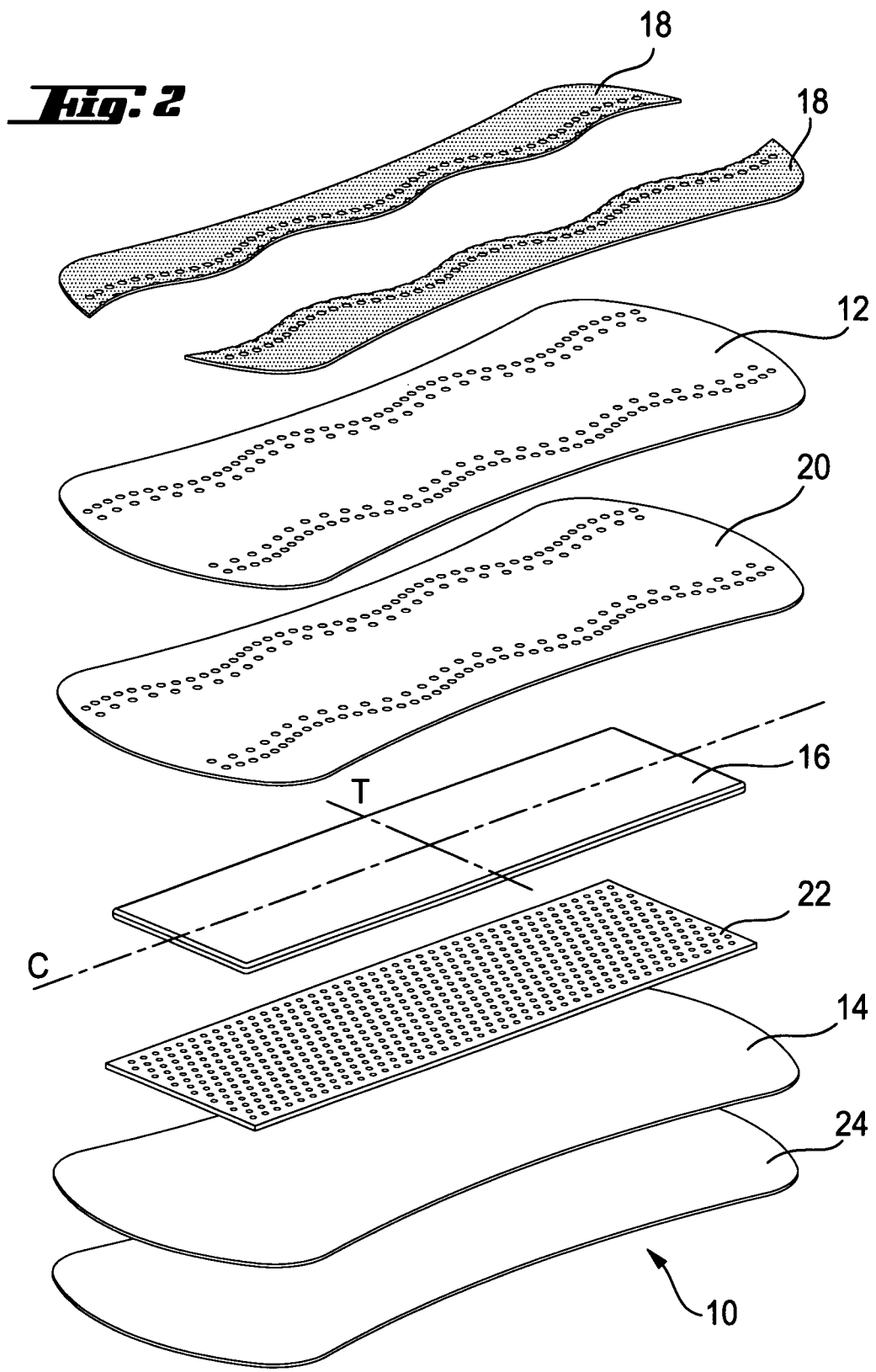
FIG. 2 is an exploded view of the article of FIG. 1.

FIG. 2 shows the different layers of the exemplary embodiment of FIG. 1. The articles of the invention normally comprise a topsheet 12, a backsheet 14, and an absorbent core 16 intermediate the topsheet 12 and backsheet 14. The topsheet wholly or partially forms the body-facing surface of the article, whilst the backsheet forms the garment-facing surface. Further additional elements to improve the performance of the articles may also be used and are represented, such as lateral topsheet strips 18, a secondary topsheet 20, and/or a secondary backsheet 22. The article may also comprise a release paper 24.

The dimensions of the feminine hygiene articles of the invention should be adapted for the use intended. For example, pantyliners ("liners") are generally smaller and compacter than pads. The thickness of the absorbent articles is usually of from about 2 mm to about 50 mm. Thin sanitary napkin articles can have a thickness of less than 6 mm, or even less than about 4 mm.

The term "longitudinal centerline" refers to the imaginary line centered between the longitudinal side edges of the article and which is generally aligned with the vertical plane which bisects a standing wearer into left and right body halves and is represented by the line C on the drawings. The term "transverse centerline" refers to the imaginary line T centered between the transversal side edges of the article and which is perpendicular to the longitudinal centerline. The length L of the article along the longitudinal centerline of the article may be between 10 cm and 25 cm, and also between 12 cm and 21 cm. The width W of the article along the transversal centerline may be between 3 and 10 cm, for example between 4 and 7 cm. All these dimensions are merely indicative and not limitative, because the normal dimensions of these and other types of absorbent sanitary articles may differ, as is known in the art.

Body-Facing Surface

Figure 3:
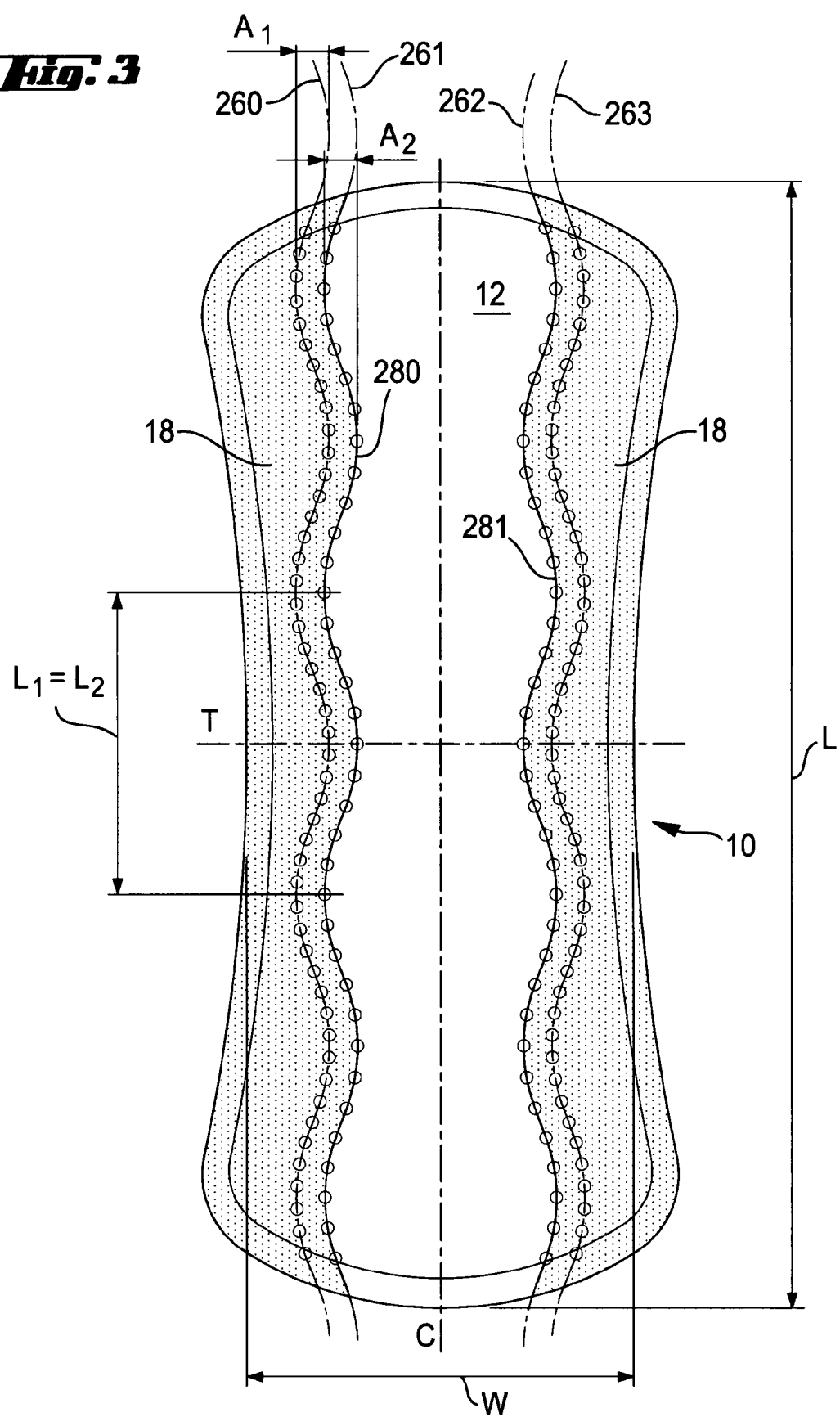
FIG. 3 is a top view of the body-facing surface of the embodiment of FIG. 1.

As shown in FIG. 3 and following, the articles of the invention have a generally flat body-facing surface, which normally may enter at least partially in contact with the user's body when it is worn. The body-facing surface of the article is normally partially or totally formed by the topsheet layer 12 of the article. In addition, the body-facing surface may further comprise two lateral topsheet strips 18, each placed along one of the longitudinal sides of the body-surface of the article, atop the topsheet 12.

Typically, the body-facing surface area of feminine hygiene articles is of at least about 50 square centimeters to prevent discharged liquids from missing the target area, although some "micro" products may have a smaller surface area (e.g. 30 cm$^2$).

Wavy Patterns

The articles of the invention comprise at least one embossed wavy pattern 26X (X being 0, 1, 2, 3, 4 or 5 in the drawings) and at least one non-embossed wavy pattern 28Y (Y being 0 or 1 in the drawings). By "wavy pattern" we mean a visually discernible form having the general aspect of a wave propagating in the longitudinal direction of the article. All kind types of waves may be used, such as sine waves, sawtooth waves, square waves, etc. . . . although waves which are smooth i.e. without sharp angles, such as sine type waves are preferred. The wavy pattern has alternating crests (hills) and troughs (valleys). By "wavelength" we mean the distance between two contiguous crests or two contiguous troughs. By "amplitude" we mean the difference in height between one crest and a contiguous trough.

The wavy patterns may be regular, by which we mean that a periodic pattern where the wavelength and amplitudes remain constant, such as a simple sine function as is represented on FIG. 3 for the embossed patterns 260, 261, 262, 263 and the non-embossed patterns 280, 281. The wavy patterns may also be non-regular periodic, for example the wavelength may be shorter in one part of the article than the other, or the amplitude may vary but this is not preferred. The amplitude and wavelength for each wavy pattern may remain substantially constant along the length of the wave, as represented in FIG. 3, or may vary at different points of the wave. By "maximum wavelength" we mean the longest wavelength measurable on the article. By "maximum amplitude" we mean the largest amplitude measurable on the article.

The wavy patterns may be continuous, i.e. without showing any interruption, or may be discontinuous, as shown on FIG. 3 for the embossed patterns 260, 261, 262, 263. A discontinuous pattern may be for example made of dots, broken lines or other interrupted elements. The number of elements per unit length does not need be constant but may vary along the length of the pattern or across the different discontinuous patterns when more than one are present. For example, on FIG. 3 the embossed patterns 260, 263 and 261, 262 have different numbers of embossed elements per unit length. Both the embossed wavy pattern and the non-embossed wavy pattern should be visually discernible on the body-facing surface of the article. Thus the patterns are preferably recognizable by an individual having a good vision (10 for each eye) when holding the product at a distance of 50 cm from the eyes under a normal incandescent lighting (e.g. under a 100 W light bulb in an average sized room).

The wavy patterns according to the invention (whether embossed or non-embossed) may or may not extend along the whole length of the article. The wavy patterns preferably extend substantially along the whole length L of the article in the longitudinal direction, as represented in FIG. 3.

The invention requires at least one embossed wavy pattern 26X and at least one non-embossed wavy pattern 28Y on the body-facing surface of the article, although it may be preferred to have an even number of embossed wavy patterns so that they can be arranged symmetrically on both side of the longitudinal centerline C. For example the article represented on FIG. 3 comprises four embossed wavy patterns 260, 261, 262, 263, which are arranged as pairs 260, 261 and 262, 263 on each side of the longitudinal centerline L. Similarly the article of FIG. 3 comprises two non-embossed wavy patterns 280, 281 symmetrically arranged on each side of the article.

In the embodiment of FIG. 3, the two embossed wavy patterns 261 and 262 are superposed with the wavy non-embossed patterns 280 and 281 respectively in the registered (optimal) situation.

Figure 4:
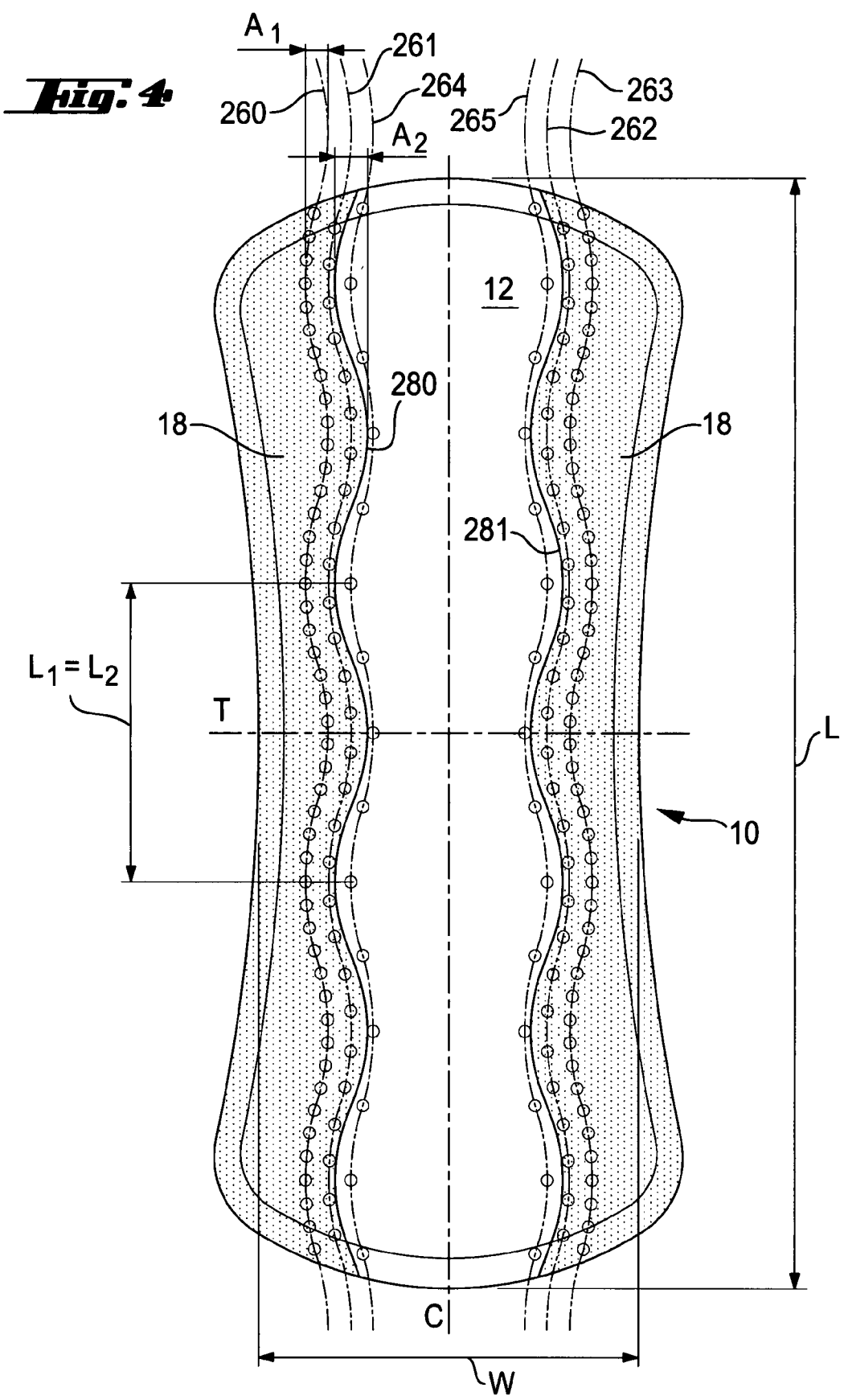
FIG. 4 is a top view of the body-facing surface of an alternative embodiment.

It may also be possible to have only one wavy pattern of each type, for example in a central position across the centerline if an impression of symmetry is to be given to the article. It may also be possible to have more than two embossed wavy patterns on each side of the longitudinal centerline, for example three on each side, as represented in FIG. 4. The longitudinal centerline L of the article may be, at least approximately, as an axis of symmetry for the body-facing surface of the article.

The embossed wavy pattern of the invention has a maximum wavelength L1 and maximum amplitude A1. The value of the ratio of the maximum wavelength L1 to the length of the article L along the longitudinal centerline (L1/L) is less than 1, and the value of the ratio of the maximum amplitude to the width of the article along the transversal centerline (A1/W) is less than 0.3. When the article comprises more than one embossed wavy pattern, at least one of these should fulfill the above requirements. The ratio L1/L is preferably less than 0.5, or even of from 0.1 to 0.3. The ratio A1/W is preferably of from 0.03 to 0.2. As discussed above, the embossed wavy patterns shown in the Figures are regular periodic and therefore their wavelength and amplitude does not vary along the length of each pattern but this is not necessarily the case.

Feminine hygiene articles with various embossments have been proposed in the past and the embossing technique is well known for this type of products. Embossing normally serves a dual function: first to provide aesthetic appeal and second to provide a bonding between the layers, in particular bond the lateral topsheet strips (when these are present) with the topsheet or the topsheet with the secondary topsheet strips. Suitable embossing can be achieved with standard techniques such as thermal, ultrasonic or pressure bond, or a combination of these. A suitable process is thermal bonding wherein the layers are passed through two steel rolls where one is engraved with the visual pattern and the other is flat. Both rolls are warmed to temperature suitable to melt the layer (typical range from 90 to 170° C.).

The articles of the invention comprise on their body-facing surface at least one non-embossed wavy pattern 28Y, which may be a colored pattern. The non-embossed wavy pattern of the invention has a maximum wavelength L2 and a maximum amplitude A2. The value of the ratio of the maximum wavelength L2 to the length of the article L along the longitudinal centerline L2/L is less than 1, and the value of the ratio of the maximum amplitude A2 to the width of the article W along the transversal centerline A2/W is less than 0.3. When the article comprises more than one non-embossed wavy pattern 28Y, at least one of these should fulfill the above requirements. The ratio L2/L is preferably less than 0.5, or even from 0.1 to 0.3. The ratio A2/W is preferably of from 0.03 to 0.2.

The non-embossed wavy pattern(s) may be formed by the wavy edge of a layer of the article, for example the inwardly facing edges of the lateral topsheet strips 18 when present, as is represented on FIG. 3, or by other means. For example one or more non-embossed, colored, lines may be printed on the article, either directly on the body-facing surface of the article (LTS or TS) or even on an underlying layer (e.g. the STS) if the color is visible by transparency though the overlying layers. With the word "non-embossed" we mean that the non-embossed wavy pattern displays a visual or tactile contrast with the rest of body-facing surface which is not due to an embossment. For feminine hygiene articles which are substantially white, as it is traditionally the case, the non-embossed pattern may be a colored pattern, realized by any shade of black, gray, blue, red, green, yellow, violet or any other colors, or tints. Recently, colored feminine hygiene articles have been proposed which can be worn with garments having a matching color, and in these cases the non-embossed wavy pattern may be white over a colored background. Some treatments of a portion of the surface of the article may also give it a visually distinctive appearance without changing its color, for example chemicals may be used to give a contrasting brightness or matteness to the surface of the article and this may create a non-embossed pattern as intended in the present invention. The non-embossed wavy pattern may also be formed by using a material having a different tactile sensation as the rest of the body-facing surface of the article, such as a different texture or thickness.

In a preferred embodiment, discussed in further details below, non-embossed wavy patterns may be formed on each side of the longitudinal centerline by colored lateral topsheet strips having a wavy cut on their inwardly facing edges.

The articles of the present invention comprise at least one embossed wavy pattern and at least one non-embossed wavy pattern, but may comprise more such patterns as long as at least one embossed and at least one non-embossed wavy pattern have the geometric properties claimed. Preferably all the wavy patterns present on the body-facing surface of the article have the claimed properties.

Figure 5:
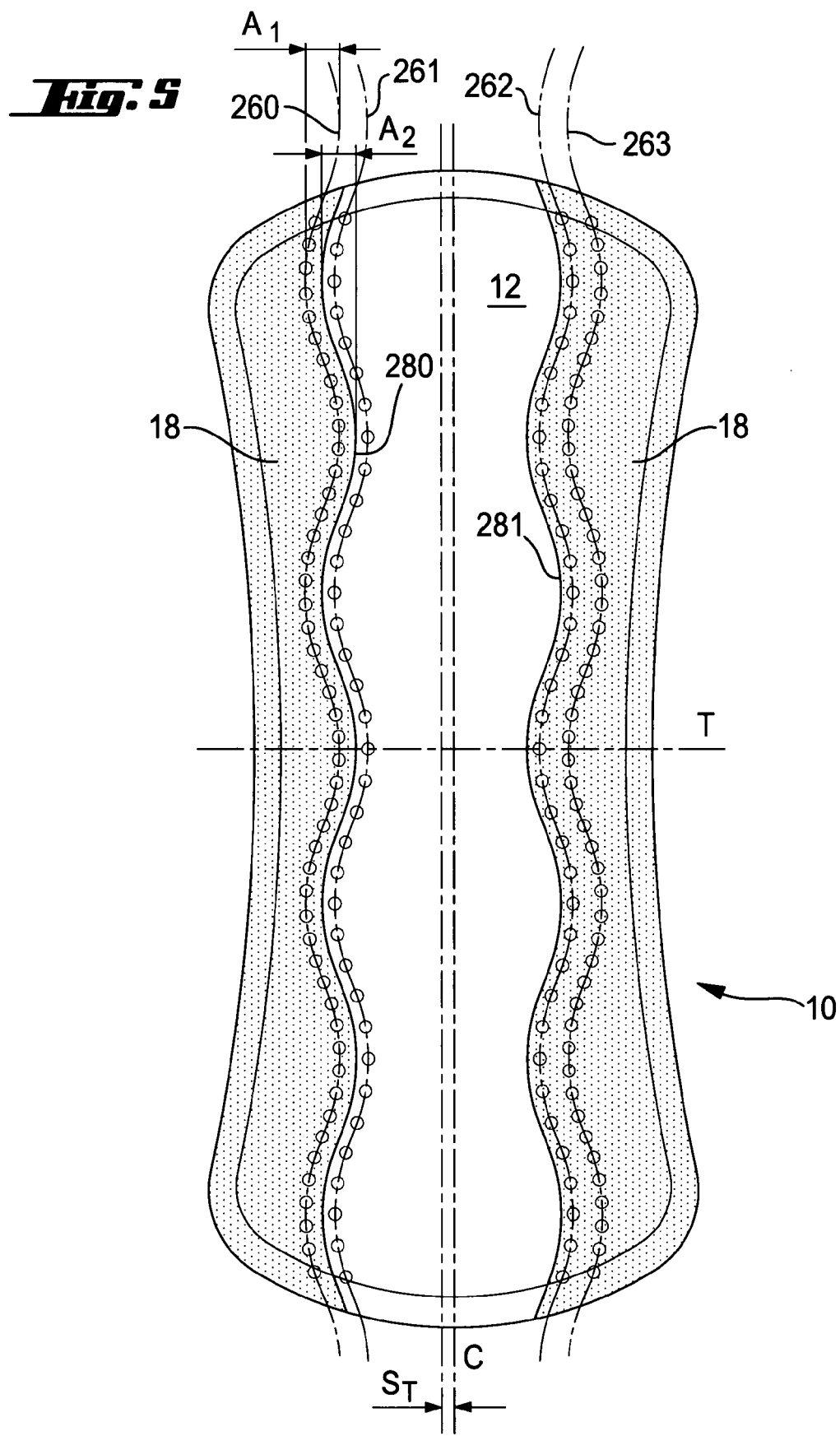
FIG. 5 is a top view of the body-facing surface of the embodiment of FIG. 1 wherein a slight shift in the longitudinal direction occurred.

The article represented on FIG. 3 comprises registered wavy patterns, as embossed and non-embossed patterns are in phase and perfectly symmetrical relative to the centerline C. As discussed above, during the high speed processing of modern production chain, it is easy for these patterns to lose their registration (i.e. their intended placement). FIG. 5 shows the result of such a small transversal displacement $S_T$, or shift, of the lateral topsheet strips 18. While the distance between the two lateral topsheet strips remained constant, their relative position has slightly shifted in the transversal direction to the left so that the non-embossed wavy patterns formed by the inwardly-facing edges of the lateral topsheet strips are no longer registered with the embossed patterns 260, 261, 262, 263. However it was found that the article still keeps a visually pleasing appearance for the user. FIG. 5 shows the result of an additional displacement or shift $S_L$, this time upwards in the machine direction axis. This displacement has little impact in the consumer acceptance of the product, thanks to the parameters chosen for these wavy patterns.

FIG. 7 shows another possible configuration wherein the wavelength L1 of the embossed patterns 26X is different from the wavelength L2 of the non-embossed pattern 28Y. In the embodiment of FIG. 7, L1 is inferior to L2, but the opposite relation may used in other embodiments. In one embodiment the value of L1 is equal to ±50%, or even ±20% of the value of L2, but other values outside this range may be used. When L1 is substantially equal to L2 as shown in FIG. 3, it may be decided to phase both embossed and non-embossed wavy patterns as shown, or these wavy patterns may also be de-phased, by a given value (for example half a wavelength) or may be randomly de-phased. Similarly, the value of A1 may be selected to be equal to ±50%, or even ±20%, of the value of A2 or be substantially the same value. The values for A1 and A2 may also be different such as A1 being inferior or superior to A2 by more than 50%.

Topsheet

The topsheet is a layer of the article that contacts the body of the wearer and receives bodily discharges. The topsheet is liquid pervious and may be flexible and non-irritating to the skin. The term "liquid pervious" as used herein refers to components that allow liquids to pass therethrough without significantly retarding or obstructing the transmission of such liquids therethrough. As used herein the term "flexible" refers to materials which are compliant and readily conform to the shape of the body or respond by easily deforming in the presence of external forces. Components are considered absorbent if such components not only transmit such liquids, but also can retain a portion of the liquids deposited on such components.

Any conventional topsheet materials may be used within the invention. Preferably the topsheet is not noisy, to provide discretion for the wearer. The topsheet should be sanitary, clean in appearance and somewhat opaque to hide the bodily discharges collected in and absorbed by the core. Suitable topsheets may be made from nonwoven materials or perforated polyolefinic films.

If desired, the topsheet may be sprayed with a surfactant to enhance liquid penetration to the core. The surfactant is typically non-ionic and should be nonirritating to the skin. A surfactant density of about 0.01 milligrams per square centimeter of topsheet area is normally suitable. A suitable surfactant is sold by the Glyco Chemical, Inc. of Greenwich, Conn. as Pegosperse 200 ML.

The topsheet may have a plurality of apertures to permit liquids deposited thereon to pass through to the core. An apertured polyolefinic film topsheet having about 5 to about 50 percent open area, typically about 25 percent open area, and a thickness of about 0.01 to about 0.03 millimeters prior to aperturing and about 0.42 to about 0.51 millimeters after aperturing is usual.

Lateral Topsheet Strips

The articles of the invention may comprise a pair of nonwoven lateral topsheet strips 18 placed above the topsheet 12, and which may deliver cloth like, soft feeling of the article edges and improve the aesthetic of the article.

The lateral topsheet strips can for example be made of all conventional type of nonwovens, such as carded thermal bonded, spun bonded, hydro entangled, melt blown, and using all range of suitable synthetic or natural fibers such as polypropylene, polyethylene, polyester, rayon, cotton, and in a mixed form or in the form of monocomponent, bicomponent fiber. For example, Pegas a.s (Czech Republic) supplies a suitable nonwoven based of bicomponent fibers made of Polypropylene (PP) as core and Polyethylene (PE) as sheath, with a polymer ratio: PP core 70%/PE sheath 30%.

The lateral topsheet strips may take the form of two parallel strips extending substantially along the whole length of the longitudinal sides of the article. Typically, the outwardly facing edges of the lateral topsheet strips are contiguous to the longitudinal sides of the article on its periphery. The inwardly facing edge of the lateral strips can be linear or have any other shapes. In the preferred embodiment represented in the Figures, the lateral topsheet strips are made of a colored material and the inwardly facing side of the edge is cut along a wavy pattern to form the non-embossed wavy pattern of the invention. An example of suitable pigment that can be introduced in bicomponent nonwoven mentioned above is Pantone color 270 Sanylen violet PP 42000634 ex Clariant. This pigment may for example be introduced in the polypropylene master batch.

The lateral topsheet strips may be mirror image of each other relative to the longitudinal centerline C. By "mirror" image we mean that the longitudinal centerline C is an axis of symmetry for the lateral topsheet strips, at least in the registered configuration (i.e. notwithstanding accidental lateral shifts of the position of the lateral topsheet strips during the manufacture). An economical process to obtain lateral topsheet strips having a regular wavy pattern cut and being mirror image of each others is shown in FIG. 8 and FIG. 9. In this process, a standard straight band of material 26 is passed through cut unit 28, which cuts an approximately regular wavy pattern along the middle of the band 26 and forms two strips of material 30, 32 having corresponding wavy edges. By regular we mean that the wavy pattern has waves having constant wavelength and amplitude. A gap between the two strips of material may be introduced by a separating roll or bar 34. A pitching unit 36 then displaces the strip 32 by approximately half a phase relative to the other strip of material 30 so that they become mirror image of each other. This may be done by increasing the distance traveled by the strip 32 by $(2n+1)/2$ times the wavelength of the wavy pattern relative to the distance traveled by the other strip 30 (n being any integer, including the null value). The strips of material 30, 32 may then brought back into parallel running and then applied on the topsheet of the article 12 to form lateral topsheet strips 18 which are mirror image of each others. The lateral topsheet strips may be adhered to the topsheet and cut by any standard techniques such as heat embossing via an embossing roll 40 or by any other conventional means, such as gluing, heat bonding or a combination thereof.

This process is economical as it allows manufacturing lateral topsheet strips with wavy cut edges without loss of material due to the wavy cut. In a next step (not represented) the periphery of the topsheet and lateral topsheet strips may be cut and embossed to the desired shape by a die cut machine if it is not rectangular, for example as represented on FIG. 3 with concave longitudinal edges and convex transversal side edges.

The presence of lateral topsheet strips may be beneficial in a number of ways, such as improving tactile sensation, appearance and performance of the product. It was found to be particularly beneficial to provide the article with lateral topsheet strips having their inwardly facing edge with a wavy cut, wherein the lateral topsheet strips are made of a colored material to provide the article with a wavy non-embossed pattern according to the invention. The colored lateral topsheet strips can be obtained by printing the lateral topsheet strips, or including a colored pigment in the fiber master batch. For example in case of bicomponent fiber the pigment can be incorporated either in the core of the fiber or in the sheath or in both.

It may be preferred that the lateral topsheet strips are made of a material having water-repelling properties, in other words an hydrophobic material, to help preventing side leakage or re-wetting of the body facing surface of the article. Examples of hydrophobic materials suitable for the lateral topsheet strips include the synthetic polymeric materials cited above, in particular polyethylene, polypropylene and their mixtures.

In a preferred embodiment, the wavy embossed pattern(s) at least partially overlaps the lateral topsheet strips. This overlap provides for at least some bonding between the lateral topsheet strips and the topsheet. It may be preferred that a least 30% of the total surface of the wavy embossed pattern(s) overlaps the lateral topsheet strips. Higher overlapping percentages are suitable for even stronger bonding, such as at least 50% or at least 75%. It was found that when the inwardly facing edges of each lateral topsheet strips feature a wavy cut forming a non-embossed wavy pattern according to the claims, it is particularly beneficial to have at least one or more wavy embossed patterns according to the claim at least partially overlapping these lateral topsheet strips. Because of the specific geometrical features claimed for the wavy patterns, it was found that even when a mis-registration of the lateral topsheet strips and/or embossment takes place, there is still a sufficient overlapping of the wavy embossed pattern over the wavy cut lateral strips to provide satisfactory bonding between the lateral topsheet strips and the topsheet.

Absorbent Core

The articles of the invention may comprise an absorbent core 16 disposed between the topsheet 12 and the backsheet 14. As used herein, the term "absorbent core" refers to a material or combination of materials suitable for absorbing, distributing, and storing aqueous fluids such as urine, blood, menses, and other body exudates.

The size and shape of the absorbent core can be altered to meet absorbent capacity requirements, and to provide comfort to the wearer. As with the other elements of the articles of the invention, there are no particular requirements for the absorbent core and any standard liquid-absorbent material known in the art for use in absorbent articles will normally be suitable.

Non-limiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof. The core, as the article itself, may be generally planar, i.e. does not have a significant variation in thickness.

Typically the absorbent core is rectangularly shaped, for ease of manufacturing. However, the core may be differently shaped, for example there is frequently a wearer preference for an absorbent core which is narrower at the center than at the ends, to comfortably accommodate the legs, and obviate or minimize occurrences of bunching or wadding of the core. Oval shaped core have also been proposed (e.g. WO 2005/084596). Further generic and specific information regarding absorbent cores can be found for example in WO 0207662A1 and WO 09119471.

Backsheet

The backsheet 14 may be any flexible, liquid resistant, and liquid impervious material. The backsheet prevents discharges collected by and contained in the sanitary napkin, and particularly discharges absorbed by the core, from escaping the sanitary napkin and soiling the clothing and bedding of the wearer. Preferably the backsheet is not noisy, to provide discretion for the wearer. In some executions, a secondary backsheet (discussed below) may be placed intermediate the core and the backsheet to second the backsheet, for example to provide liquid imperviousness.

Any conventional backsheet materials may be used within the invention, such as polyolefinic films. The backsheet may be impervious to malodorous gases generated by absorbed bodily discharges, so that the malodors do not escape. The backsheet may or may not be breathable. A low density polyethylene backsheet about 0.01 to about 0.08 millimeters in thickness, preferably about 0.05 millimeters in thickness, is usual. A polyethylene film, such as is sold by the Tredegar Corporation of Terre Haute, Ind., under model X-813 may be used. Further, the backsheet may be made of a soft cloth like material which is hydrophobic relative to the topsheet, e.g. a polyester or polyolefinic fiber backsheet.

The topsheet and the backsheet are preferentially peripherally joined using known techniques, either entirely so that the entire perimeter of the sanitary article is circumscribed by such joinder or are partially peripherally joined at the perimeter. The term "joined" refers to the condition where a first component is affixed, or connected, to a second component either directly; or indirectly, where the first component is affixed, or connected, to an intermediate component which in turn is affixed, or connected, to the second component. The joined condition between the first component, and the second component, is intended to remain for the life of the sanitary napkin. Conversely, components are considered "removably affixed" if the components may be detached and separated from each other without destruction or unintended gross deformation of either.

Any joined arrangement that provides for capture of the core intermediate the topsheet and the backsheet and a unitary assembly is suitable. Such an assembly has two mutually opposed major faces, one defined by the topsheet and one defined by the backsheet.

The outwardly oriented (garment facing) face of the backsheet may further comprise means for attaching the sanitary napkin to the undergarment of the wearer. Pressure sensitive adhesive has been commonly found to work well for this purpose. Preferably a strip of longitudinally oriented adhesive provides good protection against either the front or the back of the sanitary napkin becoming detached from the wearer's undergarment. The adhesive strip may be continuous or intermittent. A particularly preferred arrangement utilizes two longitudinally oriented strips, one on each side of the longitudinal centerline.

The backsheet typically extends across the whole of the absorbent structure and can extend into and form part of or all of the sideflaps, side wrapping elements or wings, when present.

Secondary Topsheet

The articles of the invention may optionally comprise a secondary topsheet layer 20 intermediate the topsheet 12 and the absorbent core 16.

Such a secondary layer might be manufactured from a wide range of materials such as woven, nonwoven materials, polymeric materials such as apertured formed thermoplastic films, apertured plastic film, hydro formed thermoplastic films, porous foams, reticulated foams, reticulated thermoplastic films and thermoplastic scrims. Any material described hereinbefore for the topsheet can be used for the secondary layer. In a preferred embodiment, this secondary topsheet layer underlies the apertured topsheet on the entire surface thereof, i.e., the secondary layer extends to the periphery of the topsheet so that the secondary layer underlies the topsheet on the entire inner surface of the topsheet.

The purpose of the secondary topsheet is normally to readily transfer the acquired body fluid from the topsheet to the absorbent core, the transfer of fluid occurring not only vertically in the thickness of the secondary topsheet, but also along the length and the width directions of the absorbent product. This helps the fluid capacity of the underlying storage layer to be fully utilized. Although preferred, the presence of secondary topsheet is however optional.

Secondary Backsheet

The articles of the invention may comprise a secondary backsheet layer 22 intermediate the absorbent core 16 and the backsheet layer 14. The use of a secondary backsheet is particularly indicated in presence of air permeable backsheet. The purpose of the secondary backsheet is to retard or prevent liquid from passing from the absorbent core to the outside of the product, while allowing free air flow through it. A particularly suitable example of secondary backsheet is a resilient three dimensional polymeric web, which consist of a liquid impervious film which has apertures forming capillarity or cones. The film with capillaries or cones is oriented such us the apex of the cones face the absorbent core, this to prevent passage of fluid. The capillaries or cones can have a slanted shape in order to partly close or completely close when compressed.

Release Paper

The adhesive coated on the backsheet surface are typically provided with a protective cover, which is removed prior to use. The protective cover may be a silicone coated release paper, a plastic film or any other easily removable cover. The protective cover may be in a single piece or in a multitude of pieces, e.g. to cover the individual adhesive areas. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

Method of Manufacture

The feminine hygiene articles of the present invention may comprise the usual layers or components normally found in commercially available standard articles which may be joined together by standard means such as embossing (e.g. thermal bonding) or gluing or combination of both, and the articles may be produced industrially by conventional means. In particular the embossed wavy pattern may be applied by conventional heat embossing rolls. The non-embossed wavy pattern may be obtained by various methods as discussed above, for example by providing non-embossed lateral topsheet strips with a wavy cut on their inwardly facing edge or by printing such a pattern with an ink on the topsheet, lateral topsheet strips or secondary topsheet or any combination of them, as is know in the art. In this case the ink application step may take place on an isolated layer (e.g. the secondary topsheet) before this layer is joined with any of the other layers, or on the other hand, the ink may be applied on the layer already attached or fixed, entirely or partially, to another layer. When present the lateral topsheet strips may be obtained by conventional means (cutting) or by the process discussed above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A feminine hygiene article comprising a body-facing surface, wherein the body-facing surface has a longitudinal centerline having a length L, and a transverse centerline having a width W,
   wherein the body-facing surface comprises:
   i) at least one embossed wavy pattern comprising a plurality of embossed elements, the embossed wavy pattern comprising waves having a maximum wavelength $L1$ and a maximum amplitude $A1$, wherein the values of the ratio $L1/L$ is less than 0.5 and wherein the values of the ratio $A1/W$ is less than 0.3;
   ii) at least one colored wavy pattern, the colored wavy pattern comprising waves having a maximum wavelength $L2$ and a maximum amplitude $A2$, wherein the values of the ratio $L2/L$ is less than 0.5 and wherein the values of the ratio $A2/W$ is less than 0.3; and
   iii) a white portion adjacent the at least one colored wavy pattern;
   wherein some of the plurality of embossed elements are positioned within the at least one colored wavy pattern and other of the plurality of embossed elements are positioned within the white portion.

2. The feminine hygiene article according to claim 1 wherein the body-facing surface of the feminine hygiene article comprises a first set of the embossed wavy pattern(s) and the colored wavy pattern(s) on one side of the longitudinal centerline and a second set of the embossed wavy pattern(s) and the colored wavy pattern(s) on the other side of the longitudinal centerline.

3. The feminine hygiene article according to claim 1 wherein $L1$ is equal to $L2$ with an about ±20% margin.

4. The feminine hygiene article according to claim 1 wherein $A1$ is equal to $A2$ with an about ±20% margin.

5. The feminine hygiene article according to claim 1 wherein the embossed wavy pattern(s) and the colored wavy pattern(s) have substantially constant amplitude and wavelength values across the feminine hygiene article.

6. The feminine hygiene article according to claim 1 wherein the feminine hygiene article comprises one lateral topsheet strip on each longitudinal side of the feminine hygiene article.

7. The feminine hygiene article according to claim 1 wherein the longitudinal centerline of the feminine hygiene article is approximately an axis of symmetry for the body-facing surface of the feminine hygiene article.

8. A feminine hygiene article comprising a body-facing surface, wherein the body-facing surface has a longitudinal centerline having a length L, and a transverse centerline having a width W,
   wherein the body-facing surface comprises:
   i) at least one embossed wavy pattern comprising a plurality of embossed elements, the embossed wavy pattern comprising waves having a maximum wavelength $L1$ and a maximum amplitude $A1$, wherein the values of the ratio $L1/L$ is less than 0.5 and wherein the values of the ratio $A1/W$ is less than 0.3;
   ii) at least one colored wavy pattern, the colored wavy pattern comprising waves having a maximum wavelength $L2$ and a maximum amplitude $A2$, wherein the values of the ratio $L2/L$ is less than 0.5 and wherein the values of the ratio $A2/W$ is less than 0.3;
   wherein the feminine hygiene article comprises at least one colored lateral topsheet strip on each longitudinal side of the feminine hygiene article, and wherein the inwardly-facing edges of the lateral topsheet strips are cut according to a wavy pattern so that the inwardly-facing edge forms a wavy colored pattern; and
   iii) a white portion adjacent to each of the at least one colored lateral topsheet strips;
   wherein some of the plurality of embossed elements are positioned within the at least one colored lateral topsheet strips and other of the plurality of embossed elements are positioned within the white portion.

9. The feminine hygiene article according to claim 8, wherein at least one of the embossed wavy patterns at least partially overlaps one of the lateral topsheet strips.

10. The feminine hygiene article according to claim 9 wherein at least one of the embossed wavy pattern at least partially overlaps one of the lateral topsheet strips, and at least one other of the embossed wavy pattern at least partially overlaps the other lateral topsheet strips.

11. The feminine hygiene article according to claim 9 wherein at least 30% of the total surface of the embossed wavy pattern(s) overlaps the lateral topsheet strips.

* * * * *